United States Patent [19]

Zaiger et al.

[11] Patent Number: Plant 6,409

[45] Date of Patent: Nov. 22, 1988

[54] PEACH TREE NAMED 'TASTY ZEE'

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 12,047

[22] Filed: Feb. 6, 1987

[51] Int. Cl.[4] ..... A01H 5/00

[52] U.S. Cl. ..... Plt./42

[58] Field of Search ..... Plt./42

[56] References Cited

U.S. PATENT DOCUMENTS

P.P. 5,821 12/1986 Zaiger et al. ..... Plt. 42

*Primary Examiner*—James R. Feyrer

[57] ABSTRACT

A new and distinct variety of peach tree which has the following unique combination of desirable features that are outstanding in a new variety:

1. Firm white flesh freestone fruit.
2. Fruit having attractive red skin color.
3. Fruit with ability to store 3 weeks and maintain good flavor and eating quality.
4. Heavy and regular bearer of large size fruit.
5. Vigorous upright growth.

1 Drawing Sheet

ORIGIN OF THE VARIETY

The herein variety of peach tree was originated by us in the experimental orchard located at Modesto, Calif., as a second generation seedling of a cross between O'-Henry Peach (U.S. Plant Pat. No. 2,964) and Giant Babcock Peach (U.S. Plant Pat. No. 1,353). A large group of these second generation seedlings were grown and maintained under close observation by us and the present variety which exhibited the distinctive desirable characteristics described above was selected for asexual reproduction and commercialization.

ASEXUAL REPRODUCTION OF THE VARIETY

The new and distinct variety of peach tree was asexually propagated by budding in the experimental orchard located at Modesto, Calif. and shows that said characteristics run true to form and are established and transmitted through succeeding propagations.

SUMMARY OF THE VARIETY

The herein variety of peach tree is of large size, vigorous, upright growth, and a productive and regular bearer of large size, firm, white flesh, freestone fruit with good eating and storage quality and the fruit also having a high degree of attractive red skin color. In comparison to the Giant Babcock Peach (U.S. Plant Pat. No. 1,353), the fruit of the present variety matures 4 to 5 days earlier, has firmer white flesh and a higher degree of attractive red skin color.

PHOTOGRAPHS OF THE VARIETY

The accompanying photographs show typical specimens of the foliage and fruit of the new variety, the upper and lower surface of the foliage being illustrated, an exterior and sectional view of the fruit with a fruit divided in its suture plane to reveal flesh coloration and showing a stone remaining in place. The photographic illustrations were taken shortly after being picked at maturity (shipping ripe) and the colors are as nearly true as reasonable possible in a color representation of this type.

DESCRIPTION OF THE VARIETY

The following is a detailed botanical description of the new and distinct variety of peach tree, its foliage and fruit, based upon observation of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearing.*—Regular.

Trunk:
- *Size.*—Medium to large.
- *Texture.*—Shaggy.
- *Color.*—Brown to dull brown — (5-E-3) to (6-F-4).

Branches:
- *Size.*—Medium.
- *Texture.*—Medium rough.
- *Lenticels.*—Numerous. Medium size.

Leaves:
- *Size.*—Large. Average length — 7". Average width — $1\frac{1}{2}$".
- *Form.*—Lanceolate.
- *Margin.*—Crenate.
- *Petiole.*—Average length — $\frac{3}{4}$". Average width — 1/16.
- *Glands.*—Reniform. Number varies from 2 to 6. Average number 4. Positioned on base of leaf blade and upper portion of petiole.
- *Color.*—Upper surface — green to dark green (27-F-7) to (28-F-7). Lower surface — green to grayish green (29-E-6) to (29-E-8).

Flower bud:
- *Size.*—Medium size. Medium length.
- *Form.*—Plump.
- *Pubescence.*—Pubescent.

Flowers:

*Size.*—Large — showy.

*Blooming period.*—Mar. 1, 1985 to Mar. 8, 1985. Varies slightly with climatic conditions.

*Pollen.*—Present.

*Color.*—Pink.

Fruit:

*Maturity when described.*—Firm ripe.

*Date of first picking.*—Jul. 10, 1985.

*Date of last picking.*—Jul. 16, 1985.

*Size.*—Large. Comparatively uniform. Average diameter axially — $2\frac{5}{8}''$ to $2\frac{7}{8}''$. Average transversely in suture plane — $2\frac{3}{4}''$ to $3\frac{1}{4}''$.

*Form.*—Nearly globose — slightly flattened at stem and apex.

*Suture.*—Shallow — extends from base to apex.

*Ventral surface.*—Usually rounded, some fruit slightly lipped.

*Cavity.*—Rounded to slightly elongated in suture plane. Average depth — $\frac{5}{8}''$. Average breadth — $1\frac{1}{8}''$.

*Apex.*—Slightly retuse.

*Base.*—Retuse.

Skin:

*Thickness.*—Medium.

*Texture.*—Medium tough — tenacious to flesh.

*Tendency to crack.*—None.

*Down.*—Moderate. Medium length.

*Color.*—Cream yellow to light yellow ground color (4-A-3) to (4-A-5) most of the surface overspread with red to dark red (10-B-8) to (10-D-8).

Flesh:

*Texture.*—Firm.

*Amygdalin.*—Undetected.

*Juice.*—Moderate.

*Ripens.*—Even.

*Flavor.*—Good, sub-acid.

*Fibers.*—Small and tender.

*Color.*—White to yellowish white (2-A-1) to (3-A-2). Pit cavity red (9-B-7) to (9-A-8) red extending into flesh in some areas near the pit cavity.

Stone:

*Type.*—Freestone.

*Size.*—Large. Average length — $1\frac{1}{2}''$. Average breadth — $1\frac{1}{8}''$. Average thickness — $\frac{7}{8}''$.

*Form.*—Ovid.

*Base.*—Usually rounded. Varies from rounded to straight.

*Apex.*—Acuminate.

*Sides.*—Equal to unequal.

*Surface.*—Irregularly furrow toward apex. Pitted toward base. Ridges usually rounded.

*Tendency to split.*—None.

*Color.*—Brown (6-E-8) to (7-E-8).

Use: Dessert.

*Market.*—Local and long distance.

Keeping quality: Good.

Shipping quality: Good

The peach tree, its fruit, flowers and foliage herein described may vary in slight detail due to climatic, soil and ecological conditions under which the variety may be grown. The botanical description is that of the variety produced and grown under conditions prevailing at Modesto, Calif.

The following is claimed:

1. A new and distinct variety of peach tree substantially as illustrated and described, characterized by its large size, upright growth and being a productive and regular bearer of large, firm, white flesh, freestone fruit with good flavor and eating quality; the fruit is further characterized in comparison to Giant Babcock Peach (U.S. Plant Pat. No. 1,353) by having firmer white flesh, a higher degree of attractive red skin color and being 4 to 5 days earlier in maturity.

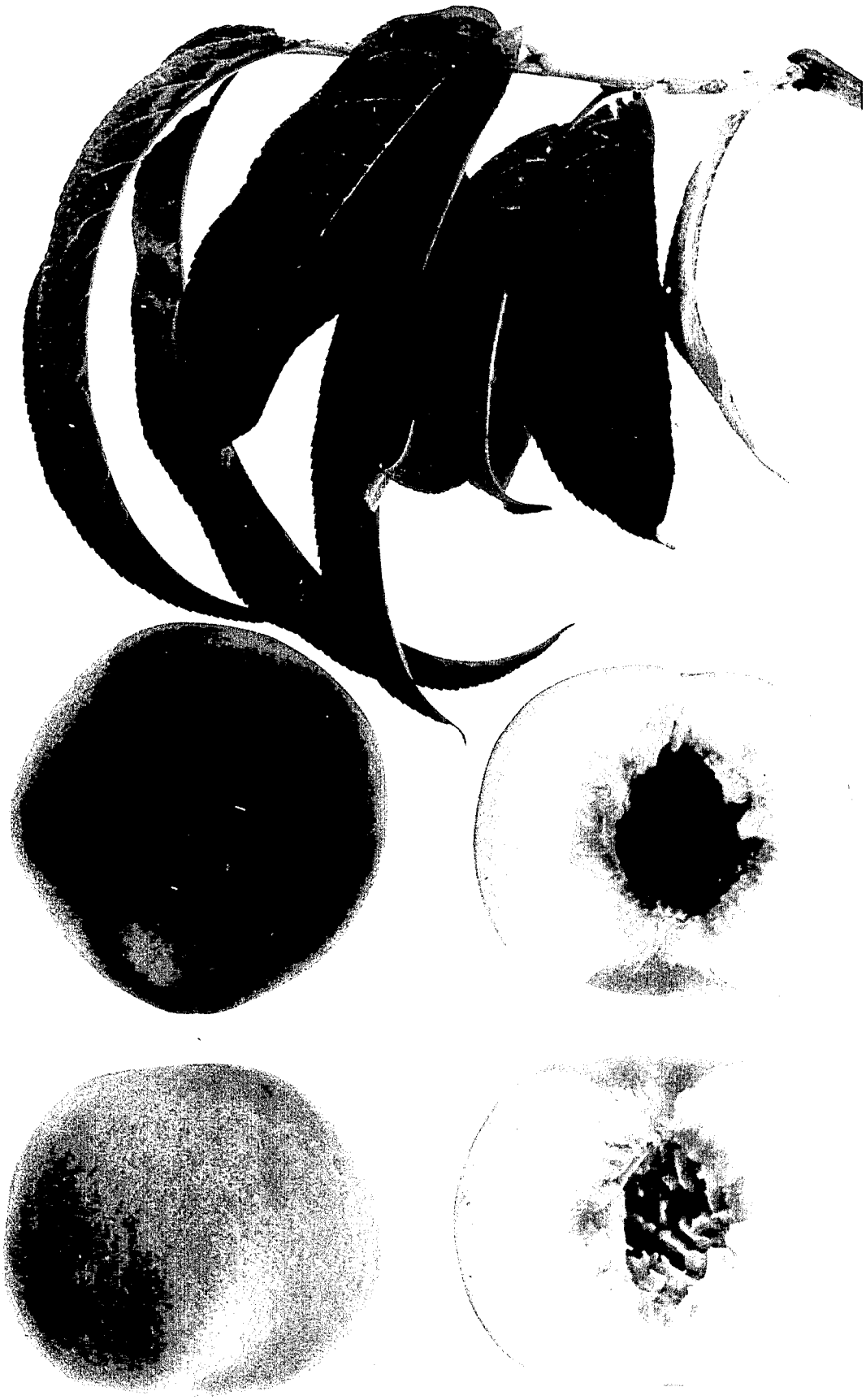

* * * * *